United States Patent [19]

Frensch et al.

[11] E Re. 30,700

[45] Reissued Aug. 4, 1981

[54] INSECTICIDAL COMPOSITIONS FOR ULTRA LOW VOLUME APPLICATION

[75] Inventors: Heinz Frensch, Frankfurt am Main; Konrad Albrecht, Fischbach; Klaus-Detlev Bock, Kelsterbach, all of Fed. Rep. of Germany

[73] Assignee: Hoechst Aktiengesellschaft, Frankfurt am Main, Fed. Rep. of Germany

[21] Appl. No.: 3,039

[22] Filed: Jan. 12, 1979

Related U.S. Patent Documents

Reissue of:

[64] Patent No.: 3,996,375
Issued: Dec. 7, 1976
Appl. No.: 536,362
Filed: Dec. 26, 1974

[30] Foreign Application Priority Data

Dec. 28, 1973 [DE] Fed. Rep. of Germany ..... 2364894

[51] Int. Cl.[3] ..... A01N 43/24

[52] U.S. Cl. ..... 424/276; 424/365

[58] Field of Search ..... 424/276, 365

[56] References Cited

U.S. PATENT DOCUMENTS

| | | | |
|---|---|---|---|
| 2,166,500 | 7/1934 | Lyman | 424/364 X |
| 3,060,085 | 10/1962 | Frensch et al. | 424/276 |
| 3,499,911 | 3/1970 | Zakary | 424/276 X |
| 3,776,857 | 12/1973 | Lindner | 252/308 |

OTHER PUBLICATIONS

Chemical Abstracts 74:124002z (1971).
Chemical Abstracts 59:5716g (1963).

*Primary Examiner*—Leonard Schenkman
*Attorney, Agent, or Firm*—Curtis, Morris & Safford

[57] ABSTRACT

Ultra-low volume formulations of endosulfan (6,7,8,9,10,10-hexachloro-1,5,5a,6,9,9a-hexahydro-6,9-methano-2,4,3-benzodioxathiepine-3-oxide), comprising endosulfan, a mixture of mono- or dicarboxylic acid (di)esters and aromatic hydrocarbons, and an epoxide stabilizer.

6 Claims, No Drawings

INSECTICIDAL COMPOSITIONS FOR ULTRA LOW VOLUME APPLICATION

Matter enclosed in heavy brackets [ ] appears in the original patent but forms no part of this reissue specification; matter printed in italics indicates the additions made by reissue.

The present invention provides ultra low volume (ULV) formulations of endosulfan (6,7,8,9,10,10-hexachloro-1,5,5a,6,9,9a-hexahydro-6,9-methano-2,4,3-benzodioxathiepine-3-oxide).

Endosulfan is known as insecticide, for example for combating cotton and rice pests and also tsetse flies. It is used in the form of emulsifiable concentrates and wettable powders which, immediately prior to application, are diluted with water and then applied in the form of the spray liquors so obtained by means of spraying apparatus. Generally, from 400 to 600 l of spray liquor per ha are employed. However, this requires large amounts of water which, especially in the tropics, often are not available. Furthermore, at elevated temperature, above all in the case of application by plane, the water content of the spray mist quickly evaporates and the active substance is frequently driven off thus resulting in uneven coverage of the treated area. It was therefore desirable to develop an endosulfan formulation that is essentially free from water. The present invention provides such a formulation, which is in the form of an ultra low volume (ULV) concentrate.

ULV application techniques are already known. In these processes liquid active substances or solutions of active substances in application amounts of from 1 to 5 liters/ha are spread by means of special nozzles. In order to attain a good and homogeneous spreading at such small amounts, the liquids have to be applied in very small droplets of from 75 to 120 microns in diameter, that is, in a far finer distribution than in the conventional spraying of emulsifiable concentrates or wettable powders. ULV formulations therefore have to contain high-boiling solvents in order to prevent quick evaporation and drift-off of the active substance and to prevent crystallization or agglomeration already in the atomizer nozzle. The flash point (closed) of these solvents should therefore be above 55° C. On the other hand, the formulation should not be too viscous, in order to ensure a good and homogeneous atomization of the composition. Although it is possible to spread products having a viscosity of up to 49 centipoises (cP), a more uniform distribution of the droplets is achieved using formulations the viscosity of which is below 20 cP. For the preparation of ULV formulations of solid substance solvents are therefore required which possesses solubility, low volatility, low viscosity and, above all, a good plant compatibility.

However, the usual paraffinic hydrocarbons and vegetable oils which answer these requirements are unsuitable because of the low solubility (5 to 8%) of endosulfan in these solvents. On the other hand the aromatic solvents generally used in emulsifiable concentrates and which are relatively well tolerated by plants, such as xylene, methylethylketone or cyclohexanone have too high volatility. Finally, high-boiling aromatic hydrocarbon fractions and high-boiling ketones such as isophorone are more or less phytotoxic; the toxicity degree rising with increasing boiling point. Furthermore, when testing solutions containing such high-boiling aromatic solvents of for instance, N-methyl-pyrrolidone, and an endosulfan content of about 25 weight %, it turned out that the active substance separated rapidly in the form of coarse crystals from the atomized droplets, thus reducing the insecticidal effect. It is therefore apparent that usual technical solvents commonly used in the preparations of the pesticide formulations do not produce useful ULV formulations of endosulfan.

It has now been found that these drawbacks can be overcome and a stable, technically applicable ultra low volume (ULV) formulation of endosulfan is obtained by combining a. 15 to 35 weight % of endosulfan;

b. 60 to 84.5 weight % of a solvent mixture consisting of 15 to 85 weight % of a liquid ester of ($C_1$ to $C_{12}$) monoalcohols with ($C_2$ to $C_{10}$) carboxylic acids, the esters containing at least 8 and, in the case of esters of a monovalent acid a maximum of 12, in the case of esters of a bivalent acid a maximum of 32 carbon atoms, and of 85 to 15 weight % of aromatic hydrocarbons having boiling ranges of from 168° to 250° C.; and c. 0.5 to 5 weight % of an epoxide as stabilizer.

Suitable esters are for example those of ($C_6$ to $C_{10}$) carboxylic acids such as caproic, capric, caprylic or pelargonic acid; or of aromatic carboxylic acids such as benzoic, toluylic, salicylic or phthalic acid. As alcohol components in these esters, there may be used for example butanol, n-octanol, i-octanol, dodecanol, cyclopentanol, cyclohexanol, cycooctanol or benzyl alcohol. Examples of suitable esters are benzyl acetate, caproic acid ethyl ester, pelargonic acid ethyl ester, benzoic acid methyl or ethyl ester, salicylic acid methyl, propyl or butyl ester, but above all diesters of phthalic acid with aliphatic or alicyclic ($C_1$ to $C_{12}$) alcohols, such as phthalic acid dimethyl, dibutyl, diisooctyl, didodecyl, dicyclopentyl, dicyclohexyl or dicyclooctyl ester. Because of its good plant compatibility, phthalic acid diisooctyl ester is especially preferred. The ester amount in the solvent mixture (b) is preferably from 40 to 80 weight %. The ester component may also be a mixture of several esters.

Preferred aromatic hydrocarbons are alkyl benzenes of 9 to 11 carbon atoms, such as the various trimethylbenzenes, methyl-ethyl benzenes, dimethyl-ethyl benzenes, diethyl benzenes, tetramethyl benzenes, trimethyl-ethyl benzenes, methyl-diethyl benzenes, pentamethyl benzene or mixtures thereof; furthermore 1- and 2-methyl naphtalene. By way of example the following technical products which essentially consist of the above compounds are mentioned. "Shellsol AB" (Shell), boiling range 187°-213° C., "Solvesso 150" (Exxon), boiling range 183°-207° C., "Aromasol H" (ICI), boiling range 168°-200° C.

The aromatic hydrocarbons are present in the solvent mixture (b) at a preferred rate of from 20 to 60 weight %.

Suitable epoxides are for example epichlorohydrin, epoxypropane, styrene oxide, phenylepoxypropane or epoxides of unsaturated vegetable oils such as linseed oil epoxide or soy bean oil epoxide. Preferably, epichlorohydrin is used in an amount of from 0.5 to 2 weight %.

The ULV formulations of the invention impart an excellent insecticidal effect to endosulfan as well as a long-duration activity, so that considerable amounts of active substance are saved as compared to the known emulsion concentrates and wettable powder formulations. For this reason, they are especially useful for combating tsetse flies in remote areas, since the application intervals may be considerably extended. The viscosity at 20° C. of such formulations is in a range of from 8 to 18 centipoises, their flash point (closed) of from 50° to 75° C. Even under tropical conditions, the products are chemically and physically stable over two years.

The following examples illustrate the invention.

EXAMPLE 1:

A 25% endosulfan ULV-formulation was obtained by dissolving 25 weight % of endosulfan in 19 weight % of Solvesso 150* and 55 weight % of phthalic acid diisooctyl ester, and adding 1 weight % of epichlorohydrine.

The flash point (closed) of the resulting mixtures is 72° C., its viscosity at 20° C. is 16.5 cP.

*Solvesso 150 has the following physical data: content of aromates 97% boiling range 183°–207° C. flash point (closed) 66° C. density 0.895 (15° C.)

EXAMPLE 2:

A 35% endosulfan ULV formulation (according to this invention) was obtained by dissolving as indicated above:

25 weight % of endosulfan in 29.5 weight % Solvesso 150 and 24 weight % of phthalic acid dibutyl ester and adding 1.5 weight % epoxylated soy bean oil.

EXAMPLE 3:

(Comparative product)

As comparative product, a commercial 35% endosulfan emulsifiable concentrate was used which had the following composition:

35 weight % of endosulfan 1 weight % of epichlorohydrine 6 weight % of emulsifiers 58 weight % of xylene.

EXAMPLE 4:

In comparison to a commercial emulsifiable concentrate containing 35% of endosulfan (EC) (Example 3), the ULV formulation of Example 1 was tested as to effect and activity period.

In a spray tower, plants of horse beans (Vicia faba) were sprayed according to the ULV process with the endosulfan 25 ULV product according to Example 1, and, for comparison, with a commercial endosulfan 35 EC emulsion according to Example 3. The plants were then kept in a moisture chamber under constant conditions (temperature 20° C., relative humidity 50–60%). The amount of product applied corresponded to a dose of 300 and 600 g of active substance/ha, respectively.

Parts of these bean plants were cut off in intervals of 1, 2, 3, 5 and 7 days and were put with the lower ends into little glass tubes filled with water. These were then placed into a paperboard cup which was covered with wire fabric, and 10 larvae of Prodenia (L 3) each (5 parallel tests) were placed onto the plant cuttings.

Examination was carried out after 3, 24, 48 and 72 hours for the plant pieces cut off the 1st day, and after 24, 48 and 72 hours for the pieces cut off later. The results of the test are apparent from the table. Concentrates according to the invention stored for 3 months at 50° C. gave the same results.

| | Conc. of | 1 day | | | | 2 days | | | 3 days | | | 5 days | | | 7 days | | |
|---|---|---|---|---|---|---|---|---|---|---|---|---|---|---|---|---|---|
| | A5 | 3 | 24 | 48 | 72 | 24 | 48 | 72 | 24 | 48 | 72 | 24 | 48 | 72 | 24 | 48 | 72 |
| Product | (g/ha) | hours | | | | hours | | | hours | | | hours | | | hours | | |
| Endosulfan | | | | | | | | | | | | | | | | | |
| 25 ULV(Ex. 1) | 300 | 20* | 84 | 90 | 86 | 86 | 86 | 82 | 72 | 72 | 78 | 70 | 70 | 68 | 45 | 49 | 53 |
| 35 EC(Ex. 3) | 300 | 10 | 38 | 38 | 38 | | not tested | | 12 | 13 | 13 | 3 | 5 | 5 | 0 | 0 | 1 |
| 25 ULV(Ex. 1) | 600 | | 82 | 88 | 88 | 84 | 82 | 92 | | not tested | | 74 | 82 | 84 | 60 | 82 | 82 |

*mortality

What is claimed is:

1. Insecticidal compositions for ultra low volume (ULV) application which comprises a. from 15 to 35 weight percent of 6,7,8,9,10,10-hexachloro-1,5,5a,6,9,9a-hexahydro-6,9-methano-2,4,3-benzodioxathiepine-3-oxide;

b. from 60 to 84.5 weight percent of a solvent mixture consisting of 15 to 85 weight percent of a liquid ester formed from a monoalcohol of 1 to 12 carbon atoms and a monovalent or bivalent carboxylic acid of 2 to 10 carbon atoms, said ester containing at least 8 and a maximum of 12 carbon atoms in the case of an ester of a monovalent acid and at least 8 and a maximum of 32 carbon atoms in the case of esters of a bivalent acid and from 15 to 85 weight percent of an aromatic hydrocarbon consisting essentially of an alkyl substituted benzene of 9 to 11 carbon atoms or a 1- or 2-methyl substituted naphthalene having a boiling range of from 168° to 250° C.; and c. from 0.5 to 5 weight percent of an epoxide selected from the group consisting of epichlorohydrin, epoxypropane, styrene oxide, phenyl epoxy-propane, and an epoxide of an unsaturated vegetable oil.

2. The insecticidal composition as defined in claim 1, wherein the solvent mixture (b) contains from 40 to 80 weight percent of the liquid ester and from 20 to 60 weight percent of the aromatic hydrocarbon.

3. The insecticidal composition as defined in claim 1 which comprises a phthalic acid diester as the liquid ester.

4. The insecticidal composition as defined in claim 1 which comprises phthalic acid diisooctyl ester as the liquid ester.

5. The insecticidal composition as defined in claim 1, wherein the epoxide is epichlorohydrin.

6. The insecticidal composition as defined in claim 1, wherein the epichlorohydrin content is 0.5 to 2 percent by weight.

* * * * *